(12) United States Patent
Krejci et al.

(10) Patent No.: US 7,811,431 B2
(45) Date of Patent: Oct. 12, 2010

(54) NANOSTRUCTURED WORKING ELECTRODE OF AN ELECTROCHEMICAL SENSOR, METHOD OF MANUFACTURING THEREOF AND SENSOR CONTAINING THIS WORKING ELECTRODE

(75) Inventors: Jan Krejci, Predklasteri (CZ); Jan Maly, Litomerice (CZ); Radka Stejskalova, Praha (CZ)

(73) Assignees: BVT Technologies A.S., Brno (CZ); Univerzita Jana Evangelisty Purkyne, Prirodovedecka Fakulta, Usti Nad Laben (CZ)

( * ) Notice: Subject to any disclaimer, the term of this patent is extended or adjusted under 35 U.S.C. 154(b) by 239 days.

(21) Appl. No.: 11/913,086

(22) PCT Filed: May 5, 2006

(86) PCT No.: PCT/CZ2006/000030

§ 371 (c)(1),
(2), (4) Date: Oct. 30, 2007

(87) PCT Pub. No.: WO2006/119716

PCT Pub. Date: Nov. 16, 2006

(65) Prior Publication Data

US 2008/0169191 A1    Jul. 17, 2008

(30) Foreign Application Priority Data

May 9, 2005    (CZ)    .................................. 2005-294

(51) Int. Cl.
*G01N 27/30*    (2006.01)

(52) U.S. Cl. .................... 204/403.01; 204/292; 204/293
(58) Field of Classification Search ................. 205/775, 205/920, 915; 204/400–435, 292, 293, 403.01; 427/77; 156/62.2

See application file for complete search history.

(56) References Cited

U.S. PATENT DOCUMENTS

| | | | | |
|---|---|---|---|---|
| 4,529,621 | A * | 7/1985 | Ballard | 438/3 |
| 6,555,159 | B2 * | 4/2003 | Clyde et al. | 427/126.3 |
| 6,686,205 | B1 * | 2/2004 | Schultz et al. | 506/12 |
| 6,764,581 | B1 * | 7/2004 | Forrow et al. | 204/403.14 |
| 7,003,340 | B2 * | 2/2006 | Say et al. | 600/345 |
| 2001/0037852 | A1 * | 11/2001 | Klemm | 156/253 |
| 2003/0108664 | A1 * | 6/2003 | Kodas et al. | 427/125 |
| 2004/0065892 | A1 * | 4/2004 | Uemura et al. | 257/99 |
| 2004/0183408 | A1 * | 9/2004 | Levy et al. | 310/365 |

FOREIGN PATENT DOCUMENTS

WO    WO 99/035312    *    7/1999

* cited by examiner

*Primary Examiner*—Ula C Ruddock
*Assistant Examiner*—Jennifer Dieterle
(74) *Attorney, Agent, or Firm*—Notaro, Michalos & Zaccaria P.C.

(57) ABSTRACT

A nanostructured working electrode of an electrochemical sensor wherein the working electrode is composed of a material in the form of a film and is inserted onto the sensor. The electrode can be prepared from materials the use of which was impossible in the working electrodes known in the art (e.g. metals of defined purity). A method of manufacturing of the nanostructured working electrode and an electrochemical sensor containing the nanostructured electrode is disclosed.

10 Claims, 3 Drawing Sheets

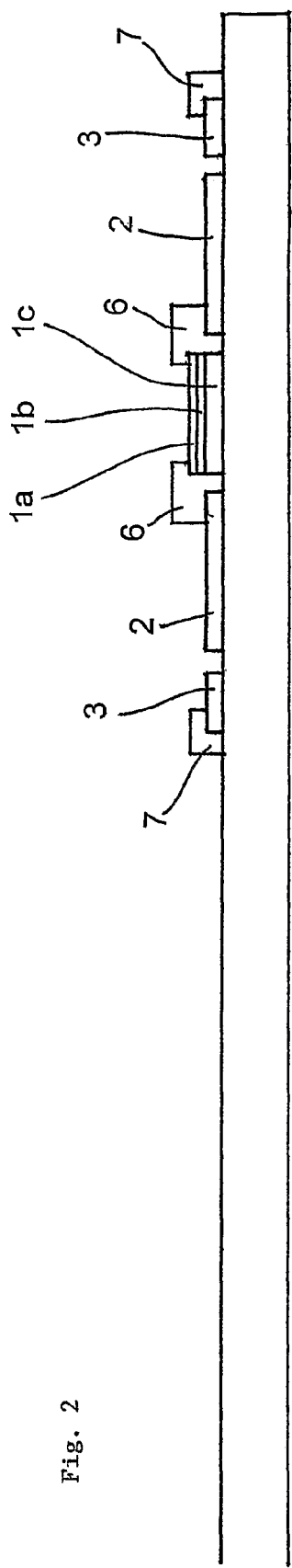
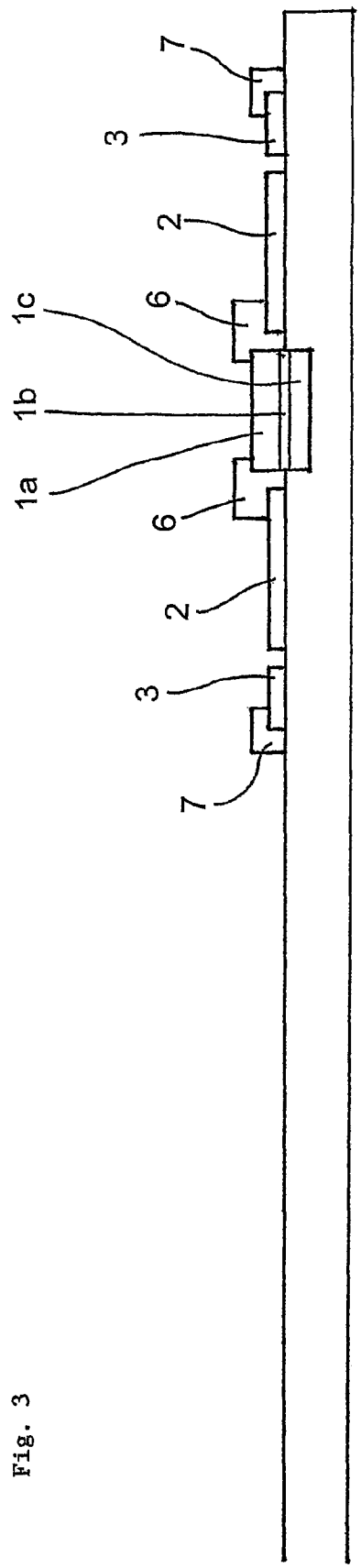

NANOSTRUCTURED WORKING ELECTRODE OF AN ELECTROCHEMICAL SENSOR, METHOD OF MANUFACTURING THEREOF AND SENSOR CONTAINING THIS WORKING ELECTRODE

TECHNICAL FIELD

The invention relates to nanostructured working electrodes of electrochemical sensors, method of manufacturing thereof and sensors containing these working electrodes.

BACKGROUND ART

Manufacture of electrochemical sensors by screen-printing is known (Czech patent 291411) and allows a cheap and effective manufacture of electrochemical sensors and biosensors. The principle of the manufacture of the working electrodes of such electrochemical sensors lies in applying pastes containing active materials by screen-printing. The active material (mostly gold, platinum, silver) is dispersed as very fine particles in a carrier, which ensures that the material is in the form of paste. This paste is applied to a suitable pad by means of printing. The paste is then hardened, optionally fired, which creates the active layer of the sensor, or the vehiculum of paste is evaporated and the active layer of the working electrode of the electrochemical sensor is then created by sintering. The disadvantage of this method is not only the porousness and the complexity of the surface structure of the printed layer, but also the fact that the carrier material can strongly influence the detection properties of the electrode. The final functional properties of the working electrode are determined by hardening of the binder or by sintering the paste particles. In all cases, the relief of the particles is transferred into the topography of the surface of the working electrode. However, in some cases the quality of the surface is crucial for the final application of the electrode.

The method of the preparation of the working electrode as described above is advantageous in the applications in which a large area of the working electrode of the sensor is needed. However, in many applications the porousness and the complexity of the surface structure of the printed layer is disadvantageous, especially when the surface of the working electrode is modified with bioactive substances such as antibodies or DNA segments. In case of DNA segments the inhomogeneities of the surface directly influence the reproducibility of the hybridization process. A further disadvantage of the working electrodes with a complex surface structure is the fact that in some cases the immobilized biochemical layer can distinctively inhibit the mass transfer between the environment, the bioactive layer of the sensor on the working electrode and the working electrode itself.

Several methods of enhancing the structure of the electrode are known in the art. One of them is described in EP 1300897, where a more homogenous nanostructure is obtained by insertion of a nanoporous ceramic element. Another possibility is imprinting of suitable matrix, which brings the nanostructure on the electrode. EP 1342736 describes this method and suitable materials. A process of controlled sintering of the electrode from nanoparticles is described in EP 1244168 and EP 1207572. Another possibility is to apply a suitable material, which creates the required nanostructure on the surface of the electrode (mentioned in U.S. Pat. No. 6,060,121) by further technological process. Another method of enhancing the properties of the working electrode lies in the use of nanostructured filler, from which the working electrode is composed, as described in WO 98/56854. Further processes of transferring the nanostructures to the working electrode are described in U.S. Pat. No. 2004/241896 and WO 2004/052489. The processes enhancing the properties of the working electrodes as described above have also some disadvantages. However, these processes do not bring on the solution for preparing extremely homogeneous structure of the electrode surface. These methodics are expensive and it is difficult to transfer them into a mass production.

Another essential problem of the existing method of manufacturing of the working electrodes by screen-printing is that the number of materials that can be treated by the screen-printing method (i.e. as particles in a paste) is limited. There are many materials that are nanostructured—i.e. materials having periodic structures with a characteristic measure smaller than 1 µm. Electrodes in the shape of fields of pyramids having the baseline of 100 nm (CVD diamond anisotropic film as electrode for electrochemical sensing, K. L. Soh, W. P. Kang, J. L. Davidson, Y. M. Wong, A. Wisitsora-at, G. Swain, D. E. Cliffel, Sensors and Actuators B 91, 2003, 39-45). Most of these materials can be prepared only in the form of a film or very small objects that cannot be incorporated as working electrodes into the sensors by using the known technologies. Many other methods for the preparation of nanostructured materials in the form of films are known. EP 1443091 describes chemical processes and compounds enabling the preparation of nanostructured films. Various methods of the preparation of nanostructured films are described in US2002/106447, WO 99/35312, WO 01/27690, U.S. Pat. No. 6,301,038 and WO 2004/011672.

The purpose of the present invention is to overcome the disadvantages of the techniques known in the art.

DISCLOSURE OF THE INVENTION

Object of the present invention is a nanostructured working electrode of an electrochemical sensor, wherein the active surface of the electrode is composed of a material in the form of a film of the thickness of 0.1-100 µm, inserted into the place of the working electrode of the sensor.

In another aspect of the invention, the film is prepared from suitable material, such as pure metal or suitable alloy or non-metallic material. The film can be prepared from an element selected from the group containing metals of the groups IA, IIA, IIIA, IVA, VA, IIIB, IVB, VB, VIB, VIIB, VIIIB, IB and IIB of the periodic table, semi-metals and non-metallic elements of the groups IIIA and IVA of the periodic table and lanthanoids.

In a further aspect of the invention, the film can be prepared from an alloy of at least two metals selected from the group containing metals of the groups IA, IIA, IIIA, IVA, VA, IIIB, IVB, VB, VIB, VIIB, VIIIB, IB and IIB of the periodic table.

In another aspect of the invention, the film can be prepared from magnetic alloys having high permeability, for example mumetal.

In a further aspect of the invention, the film for the manufacture of the working electrode can be prepared from high-temperature superconductors.

In yet another embodiment of the invention, further structures can be applied or immobilized on the film. For example, metals or other structures can be applied onto a film prepared from dielectric or semiconducting material (e.g. metal oxides) by using the processes described in US 2002/106447, WO 99/35312, WO 01/27690, U.S. Pat. No. 6,301,038 and WO 2004/011672, or organic molecule layer can be applied onto the film by the SAM (self-assembled monolayer) method.

Further object of the invention is a method of manufacturing of the nanostructured working electrode of the electrochemical sensor of the invention, wherein planar shapes are prepared from the material in the form of a film having the thickness of 0.1-100 μm, the planar shapes being by 1-1000 μm larger than the desired area of the active surface of the working electrode. A carrier paste is applied onto the place of the working electrode on the pad, onto said carrier paste the planar shape is inserted with a micromanipulator, the working electrode is then hardened and, subsequently, a part of the surface of the working electrode is overprinted with a dielectric paste and hardened again.

The planar shapes can be prepared for example by cutting with a punch.

The carrier paste applied onto the place of the working electrode ensures the conductive connection between the contacts of the working electrode and the inserted planar active surface of the working electrode prepared from the film. The paste does not contain volatiles, the leakage of which could cause a displacement or changes in the shape of the film during the hardening process. The example of such paste is a conductive epoxide. Onto the applied carrier paste, the cut planar shape is inserted by micromanipulator, whereas the shape of the tool transferring the planar shape is adapted in such manner that the nanostructure is prevented from the deformation or that the structure of the working electrode is finished with the tool of the micromanipulator.

The carrier paste with the inserted planar electrode is hardened at the temperature 0-150° C. The manufacture is then finished by printing the dielectric layer, which covers the conductive connections, margins of the working electrode and defines the final area of the surface of the working electrode.

The fixation of the nanostructured film can be performed for example by sintering the carrier paste containing the particles of gold and/or platinum and/or silver at the temperature 350-1000° C.

If the film used for the preparation of the working electrode is too thick, in a preferred embodiment of the invention there is an undercut carved into the pad, which ensures that the working electrode is in one level with the pad and so it is possible to cover it with the dielectric paste and thus define the final active surface of the electrode.

Another object of the invention is an electrochemical sensor containing the working electrode of the invention. The reference electrode and the auxiliary electrode of the electrochemical sensor can be prepared by any of the processes known in the art, such as screen-printing (CZ 291411) or tampon printing.

The sensors with the inserted nanostructured working electrodes of the invention can be used namely in the DNA detection. Structures consisting of the fields of the electrodes of the size 10-100 nm can be prepared by the technology of the invention. DNA is immobilized onto the individual electrodes of the field. Among the electrodes, there is a free space facilitating the hybridization. By the utilization of the invention it is possible to enhance the properties of the DNA sensors.

The sensors with the inserted nanostructure working electrodes can be used also for the determination of heavy metals. The electrochemical determination of heavy metals by stripping voltammetry using mercury electrode is known in the art. Mercury is toxic, but it can be replaced by bismuth. Methods of analysis where the electrode is formed by the paste consisting of the mixture of graphite and bismuth are described in the literature, but the results are irreproducible. Electrode consisting of homogeneous layer of bismuth, which is in the form of a film inserted into the place of the working electrode of the sensor, can be prepared by the method of the invention.

The use of the bismuth (Bi) film is also an example of enhancing the purity of the electrode surface by using the method of the invention. During the preparation of the working electrode from the paste containing bismuth particles and graphite particles, organic substances from the binding material and eventually other trace impurities contained in the material are adsorbed onto the surface of bismuth particles. In fact, the history of the bismuth comprised in the paste is difficult to follow. For the preparation of the electrode by the method of the invention, the film having defined purity (e.g. 99.99%) can be used and during the whole preparation process, the active surface of the sensor gets into contact only with the teflon tool of the micromanipulator, which can be kept at such grade of purity that the purity of the working electrode remains unchanged (the resulting sensor has a defined purity of the working electrode 99.99%).

The inserted nanostructured working electrodes are suitable also for the application technology SAM (self-assembled monolayer) of organic molecule layers. The technology of the application of biochemically active particles and biomolecules on the SAM base requires extremely smooth and clean surface, which cannot be obtained by printing of the active material. Extremely smooth and clean surface can be obtained by insertion of special materials in the form of films into the place of the working electrode, some of the materials having guaranteed inhomogeneity of the surface in units of atom layers (e.g. silicon films). SAM layers for adhering of the biomolecules onto the planar electrodes can be prepared and nanostructured before the insertion into the sensor. The sensor with the nanostructured planar working electrode can be used in the electrochemical determination of the activity of immobilized biomolecules. The result of nanostructurization can be the enhancement of the transfer of the detected compounds between the biomolecule and the electrode surface, and consequently the increase of the signal and the sensitivity of the detection.

The invention also allows the preparation of the electrodes from glassy carbon, which is a suitable material for electrochemical analyses with a broad applicability. The glassy carbon cannot be prepared by printing, but it can be obtained in the form of microfilms (www.goodfellow.com).

If the preparation of active layers of the sensor from the materials such as osmium, iridium, rhodium, glassy metals or other is required, it is impossible, either for physico-chemical or for chemical reasons, to transfer these materials into the form of a paste and apply them by printing. On the other hand, all these materials can be obtained in the form of a film, and can be used as materials for the preparation of the working electrodes of the present invention. The method of the invention allows the preparation of the working electrodes from high-temperature superconductors as well.

BRIEF DESCRIPTION OF DRAWINGS

The sensor consists of a working electrode (1), which is separated from a reference electrode (2) by an annulus (6) made of hydrophobic dielectric material, and an auxiliary electrode (3), concentrically arranged around the reference electrode (2) and in part covered with a hydrophobic dielectric material (7). The working electrode consists of a printed layer (1c), defining the place of the working electrode, a layer of the carrier paste (1b) and an active surface (1a). The active surface of the working electrode consists of a circle, cut from a film of the active material. The conducting paths (4), finished by connecting spots (5), designed for connecting the working electrode, the reference electrode and the auxiliary electrode are printed by screen-printing.

FIG. 2 represents a side view of the sensor as described above.

FIG. 3 represents a side view of the sensor as described above in the embodiment wherein an undercut is carved into the pad.

EXAMPLES

Figure 1:
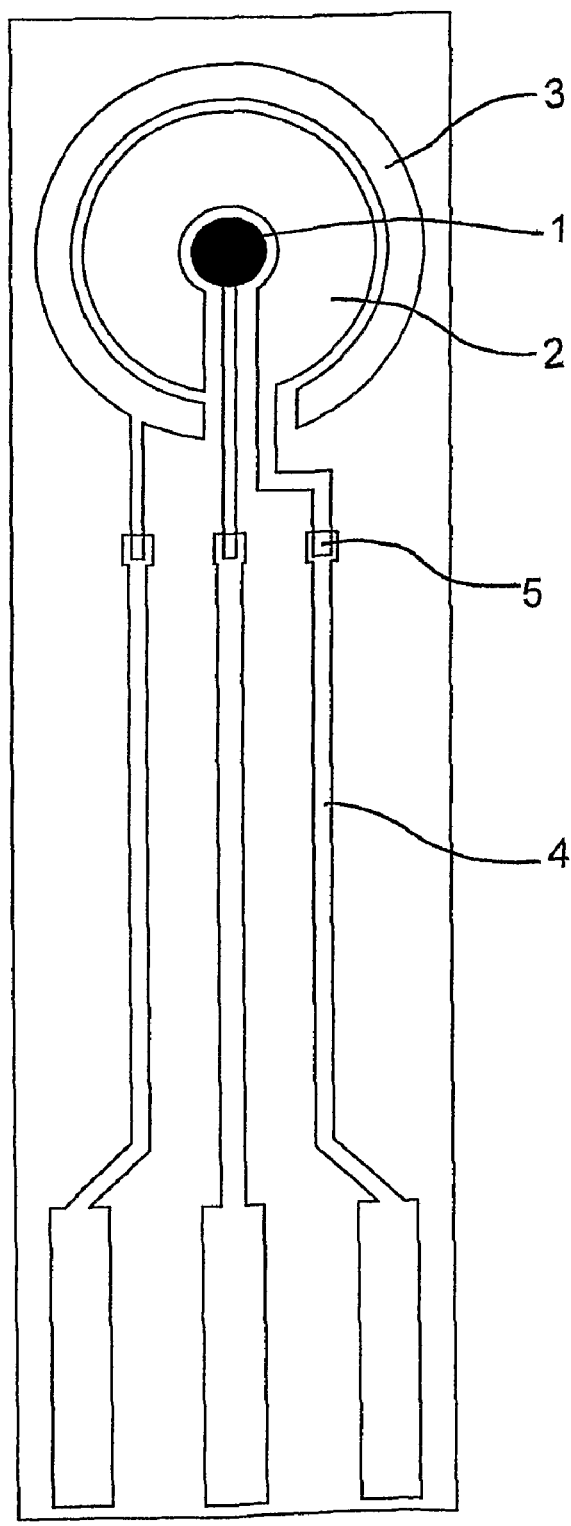
FIG. 1 represents a top view of the sensor as described above.
Figure 4:
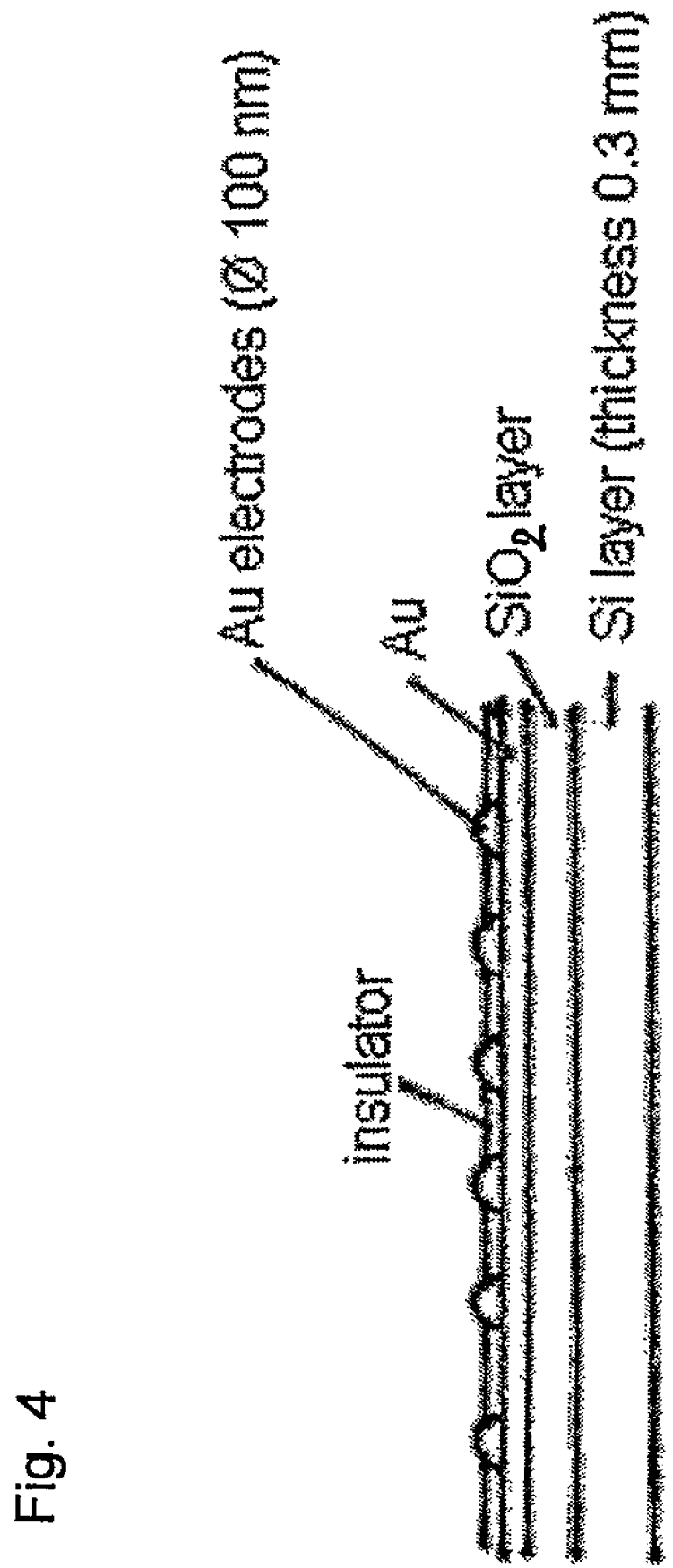
FIG. 4 represents the electrode with the field of nanostructured electrodes prepared on a silicon layer.

The invention is further illustrated by the following examples which should not be construed as further limiting.

Example 1

Conducting paths of silver are printed on a corundum pad by screen-printing, the pad is then left to rest for 15 minutes at the room temperature, dried for 15 to 20 minutes at 150±20° C. and subsequently fired at 850° C. In the next step, the working layer, i.e. the printed layer of the working electrode and the auxiliary electrode, is applied by screen-printing using an AuPd paste, then left to rest, dried and fired under the same conditions. The reference electrode is printed using Ag/AgCl. After resting, the motive is hardened at 150° C. for 15 min. A circle is cut with a punch from an Au film covered on both sides by protective films. The protective films are removed from the cut circle. Into the place of the working electrode, a polymeric paste is applied, the paste being the carrier medium for the cut circle. The circle is inserted into the place of the working electrode by a micromanipulator. The product is left to rest for 15 minutes and is dried for 15 to 20 minutes at 150±20° C. The final layer is printed using a dielectric polymeric paste. By printing this layer, the margins of the cut circle are covered. The resulting sensor is left to rest and is hardened for 60 minutes at 150° C.

Example 2

Conducting paths of silver are printed on a corundum pad by screen-printing, the pad is then left to rest for 15 minutes at the room temperature, dried for 15 to 20 minutes at 150±20° C. and subsequently fired at 850° C. In the next step, the working layer, i.e. the printed layer of the electrode of the invention and the auxiliary electrode, is applied by screen-printing using an AuPd paste, then left to rest, dried and fired under the same conditions. The reference electrode is printed using Ag/AgCl. After resting, the motive is hardened at 150° C. for 15 min. A circle is cut with a punch from a bismuth (Bi) film. The Bi film is supplied on the mylar carrier film, the other side is protected against damage during the cutting process by a protective film. Into the place of the working electrode, a polymeric paste is applied, the paste being the carrier medium for the cut circle. The protective film is removed from the cut circle. The circle is inserted with the Bi side into the place of the working electrode by a micromanipulator. The mylar film is removed. The product is then left to rest for 15 minutes and is dried for 15 to 20 minutes at 150±20° C. The final layer is printed using a dielectric polymeric paste. By printing this layer, the margins of the cut circle are covered. The resulting sensor is left to rest and is hardened for 60 minutes at 150° C.

Industrial Applicability

The sensor with the nanostructured working electrode of the present invention can be used in the chemical and food industry, in ecology for monitoring of the pollution of the environment and in medicine for inexpensive clinical analyses.

The invention claimed is:

1. A method of manufacturing of a nanostructured working electrode of an electrochemical sensor, said electrode having an active surface composed of a nanostructured material in the form of a film of the thickness of 0.1-100 µm, the method comprising: cutting planar shapes from the nanostructured material in the form of a film having the thickness of 0.1 - 100 µm, the planar shapes being by 1-1000 µm larger than the desired area of the active surface of the working electrode, applying a carrier paste onto the place of the working electrode on a pad, inserting onto said carrier paste the planar shape with a micromanipulator hardening, the working electrode and, subsequently, overprinting a part of the surface of the working electrode with a dielectric paste and hardening again.

2. The method of manufacturing of the nanostructructured working electrode of the electrochemical sensor according to claim 1, wherein the carrier paste does not contain volatiles.

3. The method of manufacturing of the nanostructructured working electrode of the electrochemical sensor according to claim 1, wherein during the first hardening step, the working electrode is fixed to the pad by sintering the carrier paste further containing particles of gold and/or platinum and/or silver at the temperature 350 - 1000° C.

4. The method of manufacturing of the nanostructructured working electrode of the electrochemical sensor according to claim 1, wherein an undercut is carved into the pad to maintain-the nanostructructured working electrode level with the pad.

5. The method of manufacturing of the nanostructured working electrode of the electrochemical sensor according to claim 1, wherein the planar shape further includes a protective layer that is removed after cutting the planar shape from the film and before inserting the planar shape with the micromanipulator.

6. The method of manufacturing of the nanostructured working electrode of the electrochemical sensor according to claim 1, wherein the film is prepared from an element selected from the group containing metals of the groups IA, IIA, IIIA, IVA, VA, IIIB, IVB, VB, VIB, VIIB, VIIIB, IB and IIB of the periodic table, lanthanoids and semi-metal and non-metallic elements of the groups IIIA and IVA of the periodic table.

7. The method according to claim 1, wherein the film is prepared from an alloy of at least two metals selected from the group containing metals of the groups IA, IIA, IIIA, IVA, VA, IIIB, IVB, VB, VIB, VIIB, VIIIB, IB and IIB of the periodic table.

8. The method according to claim 1, wherein the film is prepared from a magnetic alloy having high permeability.

9. The method according to claim 1, wherein the film is prepared from a high-temperature superconductor.

10. The method according to claim 1, wherein further structures are applied or immobilized on the film.

* * * * *